(12) United States Patent
Dellaca' et al.

(10) Patent No.: US 8,973,578 B2
(45) Date of Patent: Mar. 10, 2015

(54) APPARATUS FOR RESPIRATORY SUPPORT AND NON-INVASIVE DETECTION OF ALVEOLAR DERECRUITMENT FOR PATIENTS SUFFERING FROM RESPIRATORY FAILURE

(75) Inventors: Raffaele Dellaca', Como (IT); Antonio Pedotti, Milan (IT); Emanuela Zannin, Milan (IT)

(73) Assignee: Politecnico di Milano, Milan (IT)

( * ) Notice: Subject to any disclaimer, the term of this patent is extended or adjusted under 35 U.S.C. 154(b) by 545 days.

(21) Appl. No.: 13/433,795

(22) Filed: Mar. 29, 2012

(65) Prior Publication Data

US 2012/0266882 A1 Oct. 25, 2012

Related U.S. Application Data

(63) Continuation-in-part of application No. 12/441,183, filed as application No. PCT/EP2007/059534 on Sep. 11, 2007, now Pat. No. 8,689,787.

(30) Foreign Application Priority Data

Sep. 14, 2006 (IT) .............................. MI2006A1755

(51) Int. Cl.
*A61M 16/00* (2006.01)
*A62B 7/00* (2006.01)
(Continued)

(52) U.S. Cl.
CPC ............ *A61M 16/0051* (2013.01); *A61B 5/085* (2013.01); *A61B 5/087* (2013.01); *A61M 16/0006* (2013.01); *A61M 2016/0021* (2013.01); *A61M 2016/0027* (2013.01); *A61M 2016/0036* (2013.01); *A61M 2230/65* (2013.01)

USPC ............ 128/204.23; 128/204.18; 128/204.21

(58) Field of Classification Search
USPC ............ 128/200.24, 200.26, 204.18, 204.19, 128/204.21–204.24, 897, 898; 600/532, 600/533
See application file for complete search history.

(56) References Cited

U.S. PATENT DOCUMENTS

| | | |
|---|---|---|
| 4,972,842 A | 11/1990 | Korten et al. |
| 5,318,038 A | 6/1994 | Jackson et al. |

(Continued)

FOREIGN PATENT DOCUMENTS

| | | |
|---|---|---|
| EP | 1 551 293 | 7/2005 |
| WO | 03/103493 | 12/2003 |

OTHER PUBLICATIONS

Raffaele L. Dellacà, et al.; Lung recruitment assessed by total respiratory system input reactance; Intensive Care Med; DOI 10.1007/s00134-009-1673-3; Published on line Sep. 30, 2009.

(Continued)

*Primary Examiner* — Oren Ginsberg
(74) *Attorney, Agent, or Firm* — Ladas & Parry LLP

(57) ABSTRACT

Apparatus for respiratory support and non-invasive detection of alveolar recruitment/derecruitment provides air supply to a patient at a base pressure and an additional pressure which can be varied at a frequency of from 5 to 10 Hz and transducers applied to the conduits supplying air to the patient to send electric signals to a computer to obtain a variable positive end-expiratory pressure and a to obtain an end expiratory resistance at varying values of positive end expiratory pressure and defining the state of pulmonary recruitment as the value of the positive end-expiratory pressure which corresponds to a point of maximum expiratory resistance.

7 Claims, 5 Drawing Sheets

(51) Int. Cl.
*F16K 31/02* (2006.01)
*A61B 5/085* (2006.01)
*A61B 5/087* (2006.01)

(56) References Cited

U.S. PATENT DOCUMENTS

| | | | |
|---|---|---|---|
| 5,513,648 | A | 5/1996 | Jackson |
| 6,142,952 | A | 11/2000 | Behbehani et al. |
| 6,435,182 | B1 | 8/2002 | Lutchen et al. |
| 7,325,545 | B2 | 2/2008 | Dellaca' et al. |
| 2008/0114261 | A1 | 5/2008 | Dellaca' et al. |
| 2010/0147305 | A1 | 6/2010 | Dellaca' et al. |
| 2010/0275921 | A1 | 11/2010 | Schindhelm et al. |

OTHER PUBLICATIONS

Raffaele L. Dellacà, et al.; Optimisation of positive end-expiratory pressure by forced oscillation technique in a lavage model of acute lung injury; Intensive Care Med; DOI 10.1007/s00134-011-2211-7; Published on line Apr. 1, 2011.

Peter Kostic, et al.; Positive end-expiratory pressure optimization with forced oscillation technique reduces ventilator induced lung injury: a controlled experimental study in pigs with saline lavage lung injury; Critical Care 2011, 15:R126 http://ccforum.com/content/15/3/R126; GrisFOT3.

Ferre, R., et al. Servocontrolled generator to measure respiratory impedance from 0.25 to 26 Hz in ventilated patients at different PEEP levels.*European Respiratory Journal* (1995) vol. 8, No. 7 pp. 1222-1227.

Peslin, R., et al. "Respiratory mechanics studied by forced oscillations during artificial ventilation." *European Respiratory Journal* ((1993) vol. 6, No. 6 pp. 772-784.

Fu-Chung, Y., et al. "A Nonevasive Technique for Detecting Obstructive and Central Sleep Apnea." *IEEE Transactions on Biomedical Engineering* (1997) vol. 44, No. 12 pp. 1262-1268.

R.L. Dellaca et. al., Detection of expiratory flow limitation in COPD using the forced oscillation technique, European Respiratory Journal 2004, pp. 232-240 (9 pages total).

APPARATUS FOR RESPIRATORY SUPPORT AND NON-INVASIVE DETECTION OF ALVEOLAR DERECRUITMENT FOR PATIENTS SUFFERING FROM RESPIRATORY FAILURE

RELATED APPLICATION INFORMATION

This application is a continuation-in-part of U.S. application Ser. No. 12/441,183 filed Mar. 13, 2009, now U.S. Pat. No. 8,689,787 which is a 371 of International Application PCT/EP2007/059534 filed 11 Sep. 2007 entitled "APPARATUS FOR RESPIRATORY SUPPORT AND NON-INVASIVE DETECTION OF ALVEOLAR DERECRUITMENT FOR PATIENTS SUFFERING FROM RESPIRATORY FAILURE", which was published in the English language on 20 Mar. 2008, with International Publication Number WO 2008/031822 A1, and which claims priority from Italian Patent Application MI 2006A 001755, filed 14 Sep. 2006, the content of which is incorporated herein by reference.

FIELD OF THE INVENTION

The present invention relates to an apparatus for respiratory support and non-invasive detection of alveolar recruitment/derecruitment and distension for patients suffering from respiratory failure.

DESCRIPTION OF RELATED PRIOR ART

Respiratory failure is associated either to failure to ventilate or failure to oxygenate, which in turn can be caused by the phenomenon of the so so-called "alveolar derecruitment" (hereafter also referred to as "derecruitment").

Alveolar derecruitment consists in the alveolar spaces collapsing or filling with fluid. Alveolar collapse can be a consequence of lack of surfactant, of diffuse alveolar damage or of obstruction of the peripheral airways. Alveolar filling and consolidation are usually a consequence of inflammatory processes that cause increased permeability of the alveolar-capillary membrane and therefore to edema formation. Finally derecruitment can occur, even in healthy lungs, during the pharmacological induction of anaesthesia or paralysis and when the subject inhales oxygen enriched gas mixtures.

The parts of lung which are affected by derecruitment do not take part in pulmonary gaseous exchanges, thus causing the reduction of the oxygenation of the blood and the death of the patient.

In order to counteract this phenomenon, a ventilatory support is applied in the clinical practice, for instance by a mechanical ventilator, which ensures a so-called "Positive End-Expiratory Pressure" (also known by the acronym PEEP), with the aim of opening up the regions affected by derecruitment and holding them open and ventilated (it must be noted that hereafter the pressure is considered in relation to the atmospheric pressure and is expressed in cmH$_2$O units; "zero pressure" means "atmospheric pressure" and is equivalent to 0 cmH$_2$O; "positive pressure" means "pressure higher than atmospheric pressure").

SUMMARY OF THE INVENTION

It is the object of the present invention to obtain a non-invasive system for the detection of the variations of alveolar recruitment and lung tissue distension, so as to obtain the optimal positive end-expiratory pressure overcoming the limitations mentioned above.

According to the invention, such an object is achieved by means of an apparatus and a procedure as the attached claims.

The detection of derecruitment and the procedure for the identification of the optimal positive end-expiratory pressure (PEEP) is based of the measurement of end-expiratory reactance (Xee) and not on average inspiratory reactance.

The advantage of setting PEEP based on Xee is that in this way we can find the PEEP value that keeps the lung fully recruited at end-expiration preventing the cyclic opening and closing alveoli at each breath, which has been proved to be harmful for the lung.

The stepwise inflation series stops not necessary to a maximum value of PEEP. The endpoint is based on the detection of over distension by sampling Xee at each PEEP step. The occurrence of over distension is identified from a reduction of Xee as PEEP is increased.

The endpoint of the stepwise deflation series is not necessary a minimum value of PEEP. The endpoint is based on the detection of over distension by sampling Xee at each PEEP step. The occurrence of derecruitment is identified from a reduction of Xee as PEEP is decreased.

The advantage of determining the end-points of the optimization procedure based on the values of Xee measured at each step instead of using predetermined maximum and minimum values of PEEP is that in this way the optimization procedure is tailored on the individual patient avoiding unneeded and potentially dangerous over distension and collapse of the lung.

End-inspiratory reactance (Xei) is employed to adjust the amplitude of the pressure waveform ($\Delta P$) or the tidal volume (Vt), in order to keep Xei above a given threshold or similarly to keep the difference between Xee and Xei below a given value.

The advantage to do this is that this procedure allows to optimize more ventilator parameters and to prevent cyclic mechanical stress to the lung.

These and other features of the present invention will become more apparent from the following detailed description of an embodiment thereof, shown by no limitation in the accompanying drawings, in which

BRIEF DESCRIPTION OF THE DRAWINGS

FIG. 1 shows an apparatus 1 according to the invention, applied to a patient

Figure 1:
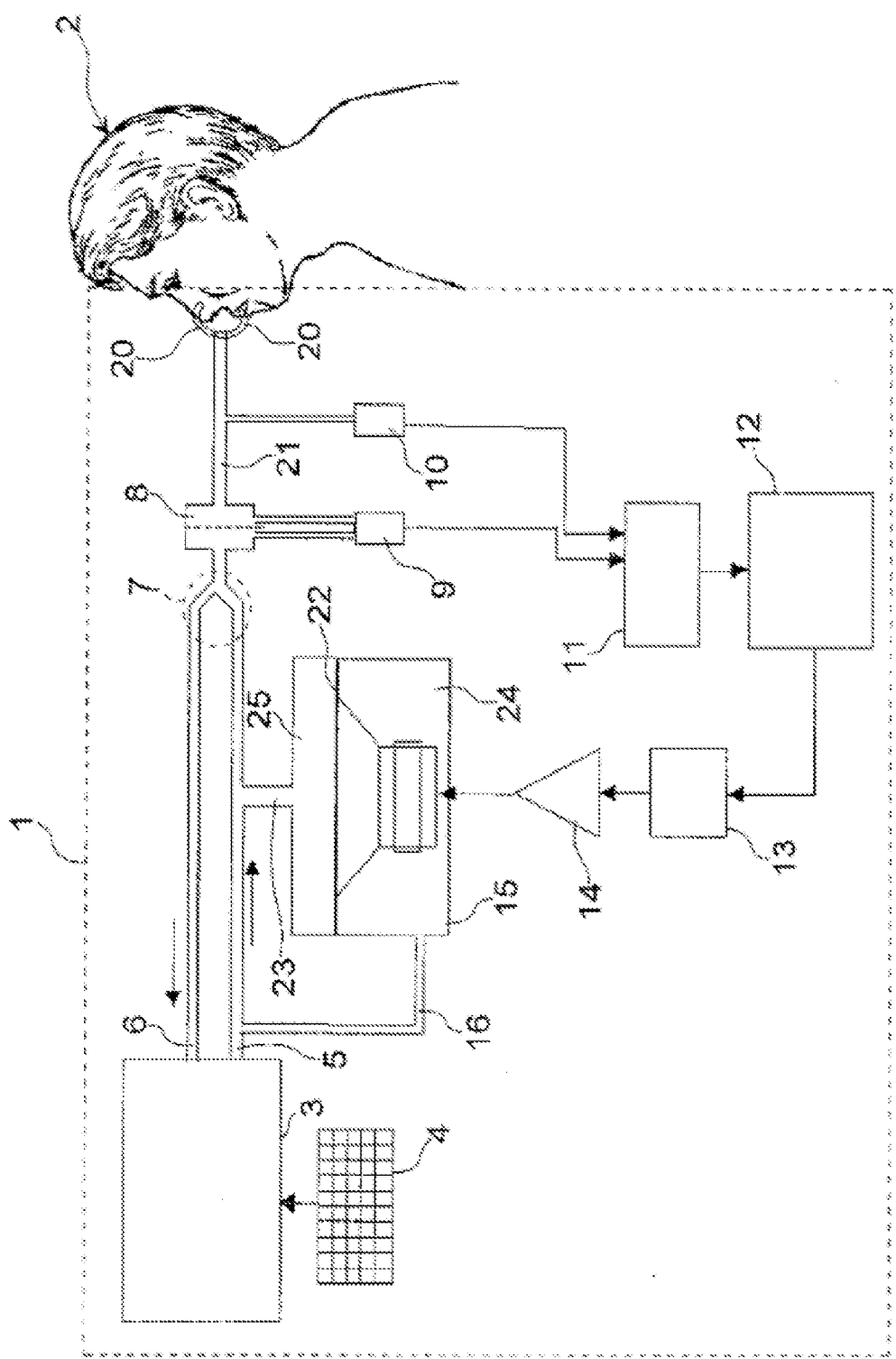
FIG. 1 shows a diagram of an apparatus according to the invention.

In this embodiment, a mechanical ventilator 3 is provided for inspiration and expiration; it also allows to impose a positive end-expiratory pressure that may be set by a human operator by means of a keyboard 4.

The mechanical ventilator 3 is connected to an inspiration tube 5, in which it pumps air directed to the pulmonary system of the patient 2, and to an expiration tube 6, by means of which the mechanical ventilator 3 allows the passive expiration of the patient and the application of a positive end-expiratory pressure. The tubes 5 and 6 are connected in the pipe fitting 7. Connectors 20 connect the apparatus 1 to the airways of the patient 2.

Downstream of the pipe fitting 7, there is a traditional pneumotachograph 8 (for instance provided with Lilly, Silverman or Fleisch resistors), allowing to convert an air flow to a pressure difference; such a pneumotachograph 8 is connected to a transducer 9 that converts such a pressure value to an electric voltage. The cascade functioning of the devices 8 and 9 thus allows to obtain a voltage proportional to the respiratory flow of the patient.

Downstream of the pneumotachograph 8 there is a traditional pressure transducer 10 that converts the pressure P to an electric voltage.

The transducers 9 and 10 are both connected to an analogue-digital convertor 11 having two inputs: in the first input there is a value proportional to the flow, in the second input there is a value proportional to the pressure. Such an analogue-digital convertor 11 provides pressure and flow values in a digital format to an electronic processor 12, which, for every sampling carried out, computes reactance and makes it available to the operator. On the basis of the data obtained, the operator modifies the positive end-expiratory pressure by means of the keyboard 4 associated to the mechanical ventilator.

The electronic processor 12 controls a speaker 15 as follows. The electronic processor 12 is connected in output to a digital-analogue convertor 13; the digital-analogue convertor 13 produces in output a voltage equivalent to the digital value obtained from the electronic processor 12.

Downstream of the digital-analogue convertor 13 there is a power amplifier 14, connected to the input of a speaker 15.

Such a speaker 15 comprises a membrane 22 that may shift (in a vertical direction with respect to FIG. 1) so as to increase or decrease the volume of the two chambers 24 and 25, separated by a membrane 22. Such a speaker 15 imposes, downstream of membrane 22 (chamber 25), a pressure component proportional to the output of the electronic processor 12.

The speaker 15 is connected to an inspiration tube 5 by means of the opening 23. In virtue of this connection, the pressure of the air inhaled by the patient 2 is subjected to an additional pressure component controlled by the electronic processor 12.

A long and narrow tube 16 is placed between the inspiration tube 5 and the chamber 24 of the speaker 15, the tube serving as a low pass filter to prevent the staving in of the membrane 22 due to excessive stresses between the chamber 25 and the chamber 24. The use of such a tube 16 is encompassed by the known technique.

Figure 2:
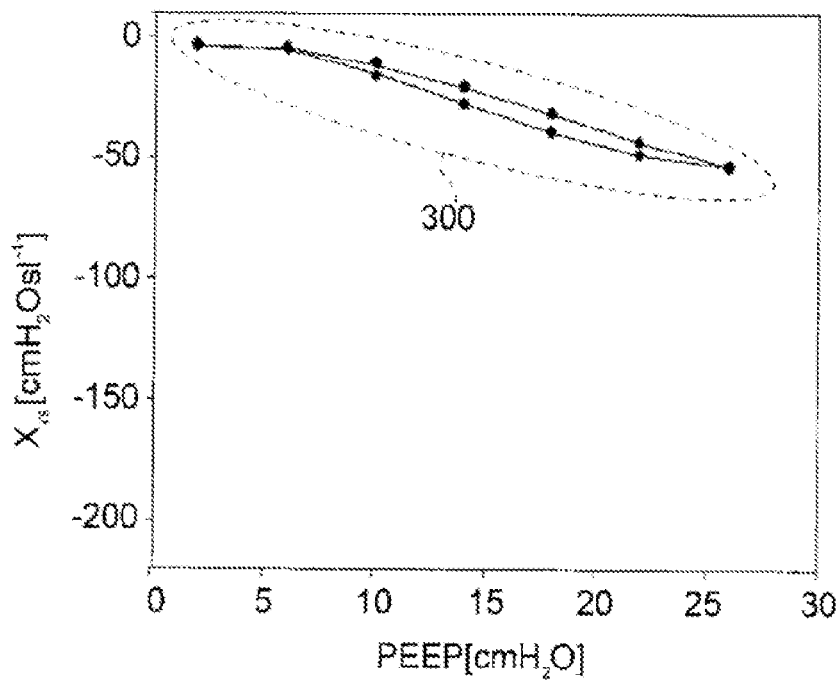
FIG. 2 shows the trend of the average reactance (Xrs) as a function of the positive end-expiratory pressure (PEEP) in a patient without recruitment.
Figure 3:
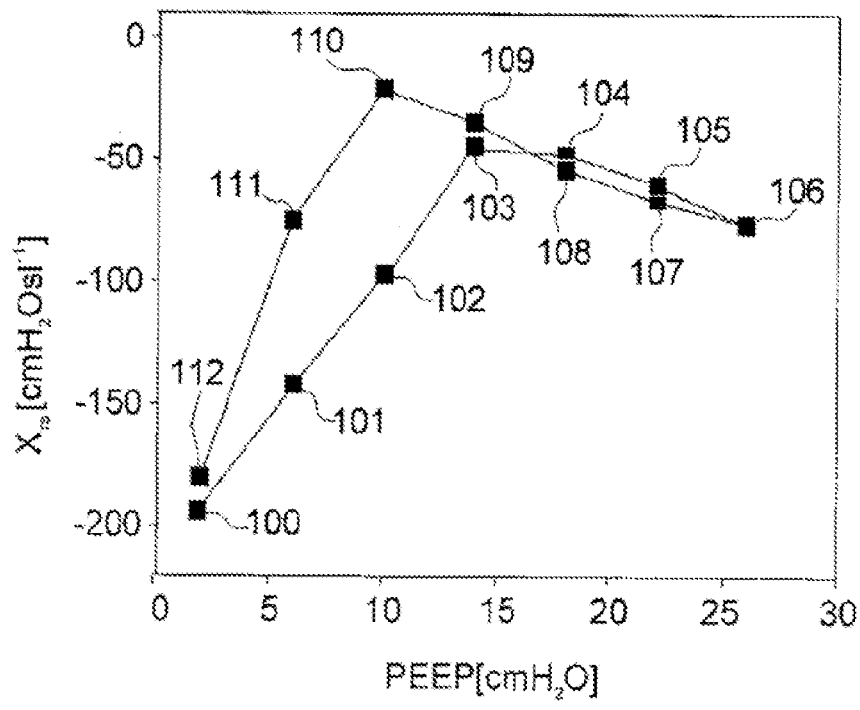
FIG. 3 shows the trend of reactance (Xrs) as a function of the positive end-expiratory pressure (PEEP) in a patient with recruitment.

FIGS. 2 and 3 are obtained during High Frequency Oscillatory Ventilation (HFOV). In this ventilation modality since the oscillator does not deliver physiological tidal volumes but only high frequency oscillations associated with very small tidal volumes, it is not possible to separate between the inspiratory and expiratory phases, and reactance (Xrs) is obtained as the average value over the period of observation.

On the contrary during conventional mechanical ventilation a proper tidal volume is delivered on top the end-expiratory pressure (PEEP), which can produce cyclic recruitment and lung tissue distension. During this ventilation modality respiratory reactance can be evaluated at end-inspiration (Xei) and at end-expiration only (Xee).

Figure 4:
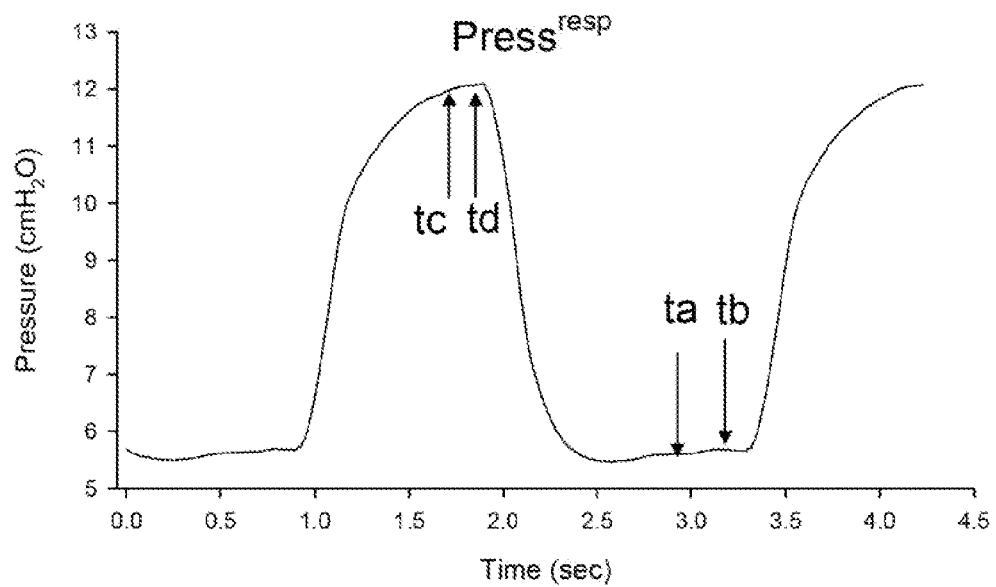
FIG. 4 shows the trend of the respiratory pressure component ($P^{resp}$) due to a mechanical ventilator in the course of time.
Figure 9:
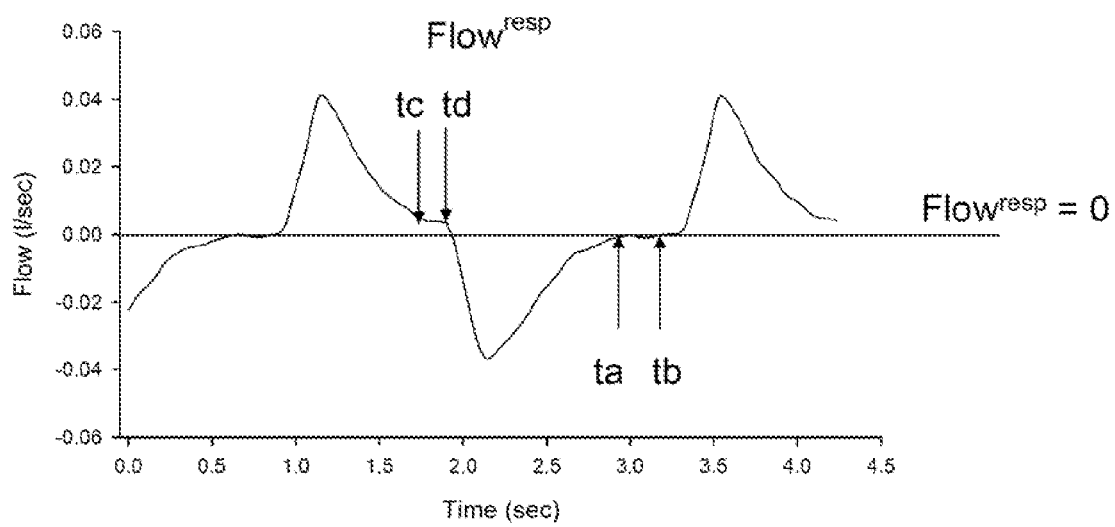
FIG. 9 shows the trend of a low frequency flow component (Flow$^{resp}$) in the course of time.

End-expiratory reactance (Xee) can be obtained as the average of reactance points measured in the period of time when respiratory flow (Flow$^{resp}$) is 0 and respiratory pressure (P$^{resp}$) is stable at positive end at end-expiratory pressure (PEEP) (period of time between ta and tb in FIGS. 4 and 9). For example ta can be picked one cycle of the stimulating pressure after the steep pressure drop (ta and tb in FIG. 6), and tb one cycle before the onset of pressure rise. The identification of this bit of the expiratory phase of the breathing cycle is particularly important when the frequency content of the respiratory components of pressure (P$^{resp}$) and flow (Flow$^{resp}$) includes the range of frequency of the stimulation signal (P$^{stim}$ and Flow$^{stim}$). A period of time of at least 3 cycles of the stimulating oscillation is required to obtain Xee. If this is not the case during the regular respiratory support the expiratory time needs to be increased or short end-expiratory pause must be performed.

Figure 6:
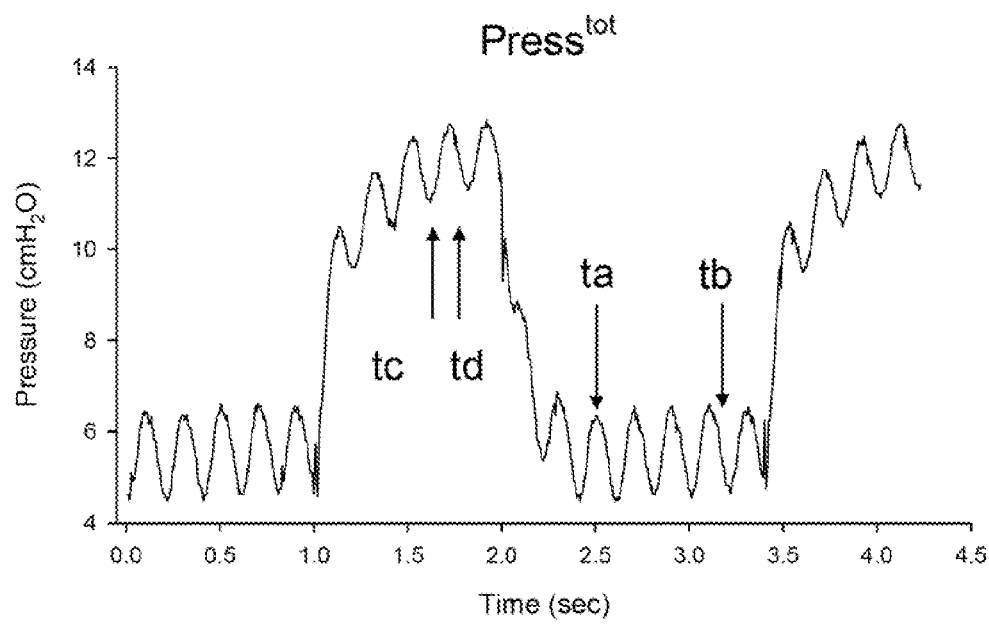
FIG. 6 shows the trend of the pressure ($P = P^{resp} + P^{stim}$) to which the respiratory system of a patient is subjected by means of a device according to the invention in the course of time.

Similarly, end-inspiratory reactance (Xei) can be obtained as the average of reactance points measured in the period of time when respiratory flow (Flow$^{resp}$) is 0 and respiratory pressure (P$^{resp}$) is stable at the maximum value (period of time between tc and td in FIGS. 4 and 9). For example tc can be picked one cycle of the stimulating pressure after the pressure has reached the maximum value and td one cycle before pressure starts to drop (FIG. 6). The identification of this bit of the inspiratory phase of the breathing cycle is particularly important when the frequency content of the respiratory components of pressure (P$^{resp}$) and flow (Flow$^{resp}$) includes the range of frequency of the stimulation signal (P$^{stim}$ and Flow$^{stim}$). A period of time of at least 3 cycles of the stimulating oscillation is required to obtain Xei. If this is not the case during the regular respiratory support the expiratory time needs to be increased or short end-inspiratory pause must be performed.

The idea of optimizing positive end-expiratory pressure (PEEP) based on the maximum of end-expiratory reactance (Xee) allows to keep lung open throughout the respiratory cycle and therefore to minimizes the cyclic intra-tidal recruitment. End-inspiratory reactance (Xei) can be evaluated in addition to end-expiratory reactance (Xee) to optimize the inspiratory pressure or the tidal volume delivered by the mechanical ventilator.

Therefore, once the maximum of expiratory reactance during the deflation (110) is known, ventilation with the positive end-expiratory pressure corresponding to such a maximum point (110) may be performed.

The value of end-expiratory reactance (Xee) may be monitored breath by breath to detect derecruitment phenomena in the course of time and identify the best moment for a new recruitment manoeuvre.

FIG. 4 shows the trend of the respiratory pressure P$^{resp}$ of a patient subjected to ventilation with positive end-expiratory pressure in the course of time; the trend of the air flow (Flow$^{resp}$) related to the same breath is shown in FIG. 9. Conventionally, the inflow into the patient is considered positive (that is, during inspiration). The measurement unit of such a flow is hereinafter liters per time unit (l/s).

The patient inhales ($Flow^{resp} > 0$) in the range of time between 0 and t1; the patient exhales ($Flow^{resp} < 0$) in the range of time between t1 and t2, and then inhales again after time t2.

It must be noted that at time t2, at the end of the expiration, the pressure is positive and equivalent to the PEEP ($P^{resp}$=PEEP>0). Without the mechanical ventilator, the respiratory pressure would be near zero, and $P^{resp}$ would be negative during the inspiratory phase.

The ventilator settings should carefully be determined in order to support the patient without causing harm to the lung. The adverse consequences of an aggressive ventilation strategy are known by the term "VILI", which is the acronym of "Ventilator-Induced Lung Injury". The positive end-expiratory pressure (PEEP) is the major parameter affecting lung volume recruitment. The rationale for the titration of this important parameter is the following: too low a pressure does not allow to open up the lung and may be associated to cyclic recruitment and derecruitment of alveolar units during tidal ventilation, whereas too high a pressure causes further damage to the parenchyma enhancing the inflammatory condition and often has very dangerous consequences for the patient. A significant source of mechanical stress and damage for the lung parenchyma is the cyclic intra-tidal recruitment and intra-tidal overinflation of alveolar units. For this reason current strategies for mechanical ventilation of patients with acute respiratory failure include low tidal volumes and high levels of positive end-expiratory pressure (PEEP) to prevent alveolar collapse at end expiration.

Currently the setting of positive end-expiratory pressure (PEEP) is based on oxygenation, which is an indirect and crude indicator of lung recruitment, and much is left to the experience and to the insight of the clinician because of the lack of non-invasive and automatic apparatuses able to quantify the presence of derecruitment and estimate how the latter may vary as the positive end-expiratory pressure (PEEP) varies.

It is well established that dynamic respiratory mechanics should be used to identify the optimal settings for respiratory support. The assessment of dynamic compliance during a decremental positive end-expiratory pressure (PEEP) trial has been successfully employed for the identification of the optimal PEEP. However this method has several limitations: i) it requires either that the patient is paralysed or the use of an esophageal balloon for the estimate of the transpulmonary pressure, ii) it is strongly affected by non-linearities of the respiratory system that are very often present in diseased lungs, iii) it is not able to track cyclic phenomena occurring during tidal ventilation.

Figure 5:
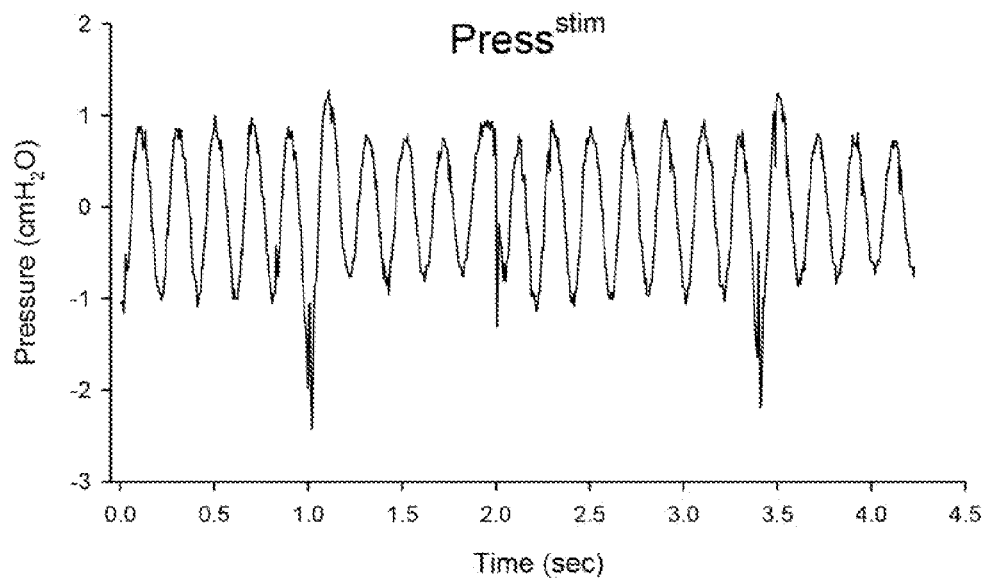
FIG. 5 shows the trend of the additional pressure component ($P^{stim}$) in the course of time.
Figure 8:
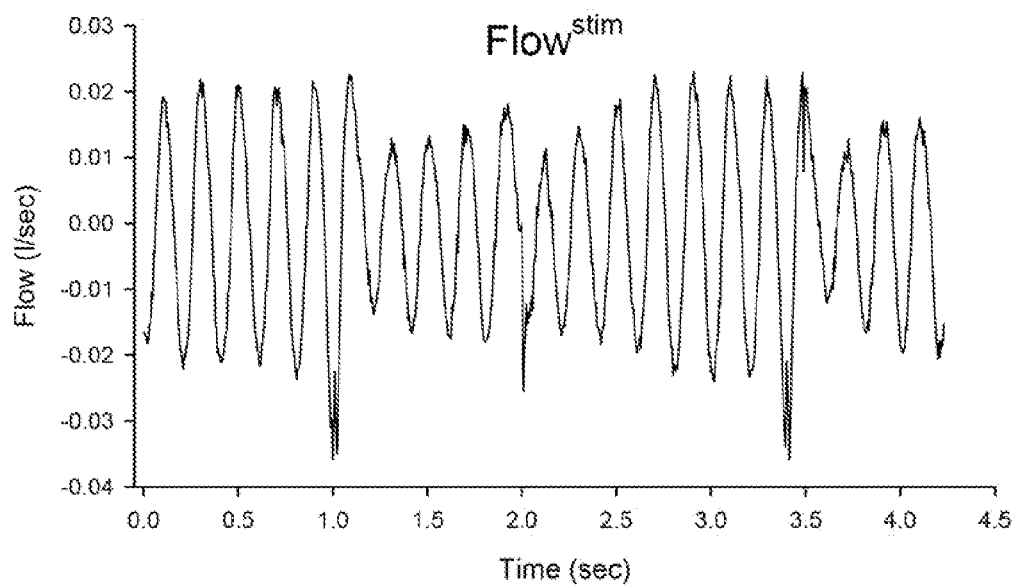
FIG. 8 shows the trend of a high frequency flow component (Flow$^{stim}$) in the course of time.

FIG. 5 shows an example of the pressure component generated by the apparatus to obtain reactance ($P^{stim}$) and the total pressure signal ($P^{tot}$) resulting from the overimposition of $P^{stim}$ on the regular respiratory signal ($P^{resp}$). FIG. 8 shows the correspondent flow signals ($flow^{stim}$, $flow^{tot}$, $flow^{resp}$) for the same respiratory cycle. The frequency of the pressure component imposed to obtain the reactance must be high enough compared with respiratory rate to allow the separation of the respiratory components ($P^{resp}$ and $flow^{resp}$) from the stimulating components ($P^{stim}$ and $flow^{stim}$) by adequate signal processing algorithms. Since the respiratory pressure ($P^{resp}$) may have harmonics in the same frequency range of the pressure component imposed to obtain reactance ($P^{stim}$), the apparatus should comprise means to generate short pauses at end-inspiration and at end-expiration (for example by increasing the inspiratory and expiratory times) in order to obtain stable estimates of the end-inspiratory (Xei) and end-expiratory reactance (Xee).

Said means allowing to carry out the respiratory functions are generally means adapted to carry out the inspiratory and expiratory operations with the possibility of imposing a positive end-expiratory pressure; they usually comprise a mechanical ventilator. The mechanical ventilator itself may also be able to generate said additional pressure.

Reactance (Xrs) can be obtained as the average of the instantaneous reactance values over a breath, or as the average over the inspiratory phase (or part of it) and of the expiratory phase (of part of it) separately, but it could also be an indicative value, for instance the maximum value, or the average value related to half a breath or even another value.

In some embodiments, the computing means automatically control the mechanical ventilator and may thus set the positive end-expiratory pressure according to algorithms adapted to determine, at least approximately, the maximum value of end-expiratory reactance (described hereafter) and the positive end-expiratory pressure associated thereto, which is the optimal positive end-expiratory pressure.

The additional pressure component ($P^{stim}$) is generally overlapped to the pressure imposed by the mechanical ventilator ($P^{resp}$) by the action of external devices, such as speakers or modulating valves (such as voice-coil actuators) or due to the mechanical ventilator itself.

The additional pressure component may also be obtained as the harmonic of an impulse or pressure. In this case, filters need to be used allowing to cut the frequencies which are too low or too high.

However, as a variant, systems based on the known art, such as systems based on the use of high frequency mechanical ventilators (HFOV), may also be used. Such a technique consists in delivering sub-physiological tidal volumes by means of the application of high frequency oscillatory pressures overlapped to a continuous distension pressure at the entrance of the airways. Such a technique is described in the paper: "High-frequency oscillatory ventilation: Mechanisms of gas exchange and lung mechanics", J. Jane Pillow, Crit. Care Med. 2005, vol. 33, issue 3 (suppl.). By means of such a technique the main ventilation parameter is the continuous distension pressure, generally known by the acronym CDP. From an operative point of view, the continuous distension pressure has the same role as the positive end-expiratory pressure (PEEP). In such systems, the frequency of the respiratory pressure is suitable to obtain reactance even without the need of further means.

The invention also relates to an automatic or manual procedure for the non-invasive monitoring of the variations of the alveolar recruitment and distension of a patient with respiratory failure.

By means of such a procedure, an additional pressure component oscillating at frequencies higher than respiratory rate is overlapped to the normal respiratory pressure imposed by a mechanical ventilator. If the spectral content of the breath imposed by the mechanical ventilator has frequency components in the range of the additional pressure oscillations short end-inspiratory and end-expiratory pauses (eg 0.5-1 sec) may be required for a stable estimate of inspiratory (Xei) and end-expiratory reactance (Xee).

An example of additional pressure component, designated by $P^{stim}$, is shown in FIG. 5. $P^{stim}$ is added up to a respiratory pressure component imposed by the mechanical ventilator. Such a component is completely equivalent to the previously described $P^{resp}$ (the symbol of which will therefore be used) and is thus shown in FIG. 4. The same considerations concerning PEEP, t1 and t2 apply thereto.

The total pressure, to which the respiratory system of a patient is subjected, designated by P and shown in FIG. 6, is therefore obtained from the sum of $P^{stim}$ (FIG. 5) and $P^{resp}$ (FIG. 4).

Figure 7:
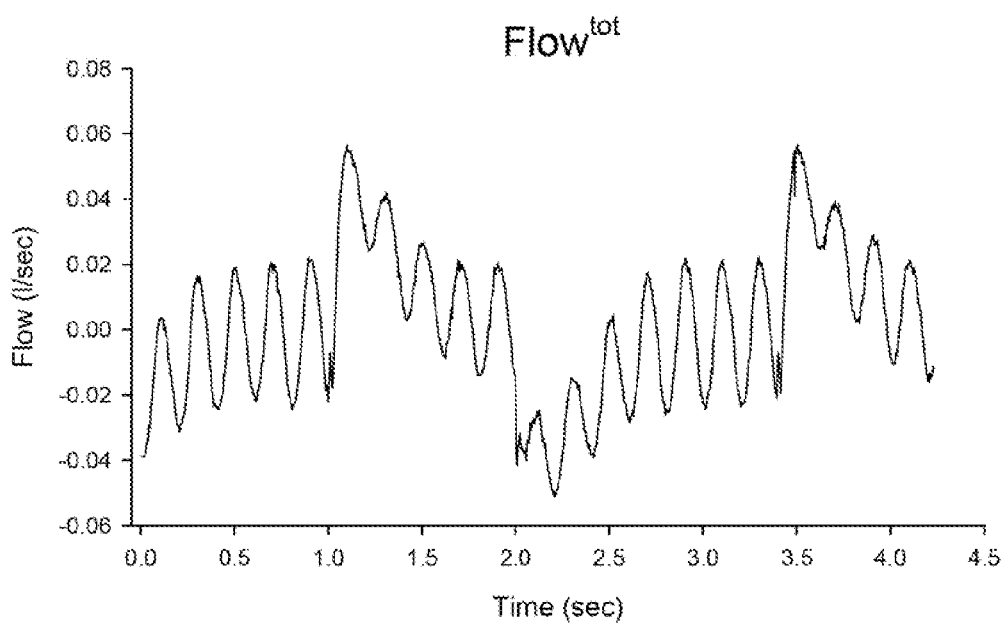
FIG. 7 shows the trend of the air flow (Flow$^{tot}$) to which the respiratory system of a patient is subjected by means of a device according to the invention in the course of time.

The high frequency flow component $Flow^{stim}$ (FIG. 8), the low frequency flow component $Flow^{resp}$ (FIG. 9) and the total flow, which is the sum of such components, Flow (FIG. 7) respectively correspond to $P^{stim}$, $P^{resp}$ and P.

It is known that an equivalence may be made between a respiratory system and an electric system, and that by the measurement of flows and pressures of the respiratory system (converted to currents and voltages in the equivalent electrical system) the trend of the input impedance of the total respiratory system may be computed, for instance as described by Dellacà, Santus, Aliverti, Stevenson, Centanni, Macklem, Pedotti e Calverley in "Detection of expiratory flow limitation in COPD using the forced oscillation technique", Eur. Respir. J 23:232-240, year 2004.

To obtain the optimal positive end-expiratory pressure, the respiratory system of a patient is initially subjected to an end-expiratory pressure which is certainly lower than the optimal positive end-expiratory pressure of the patient. Then the value of the positive end-expiratory pressure (PEEP) is increased (inflation series). The positive end-expiratory pressure (PEEP) can be either increased to a predetermined maximum value or it can be increased step-wise evaluating the response of the patient at each value of positive end-expiratory pressure (PEEP). In a derecruited lung, as positive-end expiratory pressure (PEEP) is increased reactance (Xrs) is supposed to increase until the distension of the aerated tissues becomes more relevant than the achievement of further recruitment, and therefore reactance (Xrs) starts to decrease. The reduction in reactance (Xrs) could be considered a criterion for stopping inflation. The inflation series is followed by a progressive decrease of positive end-expiratory pressure (deflation series). The end-point of deflation can be either a predetermined minimum value of positive end-expiratory pressure (PEEP) or the identification of derecruitment. At each value of positive end-expiratory pressure reactance (Xrs) is evaluated and the occurrence of derecruitment can be identified by a reduction of reactance (Xrs) compared with the previous positive end-expiratory pressure (PEEP) step, as described by Dellacà, Zannin, Kostic, Olerud, Pompilio, Hedenstierna, Pedotti, and Frykholm in "Optimisation of positive end-expiratory pressure by forced oscillation technique in a lavage model of acute lung injury" and by Kostic, Zannin, Olerud, Pompilio, Hedenstierna, Pedotti, Larsson, Frykholm, and Dellacà in "Positive end-expiratory pressure optimization with forced oscillation technique reduces ventilator induced lung injury: a controlled experimental study in pigs with saline lavage lung injury".

The reactance is designated by Xrs; it is expressed in cm $H_2O$ s/l, where s are seconds and l are liters of air. A computing method to obtain the reactance values (Xrs) will be described at the end of this description.

A graph of the resulting values of reactance (Xrs) is plotted at each step of the inflation and deflation series. FIG. 2 shows the graph 300 of a patient with a non-recruitable lung, which means that during the inflation series pressure increments are not associated to recruitment of previously collapsed alveolar units, and during the deflation series the lung does not derecruit. FIG. 3 shows the graph of a patient having derecruitment. The detection of the phenomena of recruitment and derecruitment may therefore be observed with the naked eye.

The graph of FIG. 3 is characterised by a marked hysteresis, with lower values of reactance (Xrs) during the inflation series (from 100 to 106) compared with those obtained during the deflation series (106 a 112). The value of the reactance (Xrs) obtained at lower values of positive end-expiratory pressure (PEEP) results being lower if the portion of lung affected by derecruitment is broader.

When the positive end-expiratory pressure (from 100 to 103) increases, in case of recruitment of new alveolar units, reactance progressively increases.

At a certain point, the increase of the working pressures leads to an overdistension of the lung thus causing a reduction in compliance and, therefore, reactance starts to decrease again (from 104 to 106), thus reversing the trend as a function of the positive end-expiratory pressure.

Similarly, during the deflation series (from 106 to 112), an increase of the reactance (Xrs) occurs at first (from 106 to 110), due to the elimination of the overdistension, followed by a decrease (from 106 to 112) due to the collapse of alveolar units and to the lung closing up again.

The maximum of the deflation curve (110) represents the best compromise between the recruitment of new alveolar units and the overdistension of the already open parts. The difference between the inflation series (from 100 to 106) and the deflation series (from 106 to 112) is due to the effect of the hysteresis associated to the recruitment: once the lung is opened up, lower pressures are sufficient to obtain a given degree of pulmonary recruitment with respect to those required for the opening.

Therefore, the respiration of the patient is subjected to a respiratory pressure due to two components:

a respiratory component $P^{resp}$ due to the mechanical ventilator 3;

an additional component $P^{stim}$ due to the speaker 15 controlled by the electronic processor 12.

The electronic processor 12 controls the speaker 15 so that this imposes the frequency of sinusoidal additional pressure component $P^{stim}$ at 5 Hz and the amplitude smaller than 2.5 $cmH_2O$ peak-to-peak. The frequency content of the additional pressure should be higher than the respiratory rate of the subject. If the spectral content of the pressure due to the mechanical ventilator includes the frequency range of the additional pressure component ($P^{stim}$) the expiratory time provided by the ventilator should be high enough to guarantee at least 3 cycles of the lowest frequency component of the stimulating signal ($P^{stim}$ and $Flow^{stim}$) at end-expiration (see FIGS. 5 and 8).

The procedure followed by the operator for the titration of the ventilator settings is as follows:

setting of the positive end-expiratory pressure (PEEP) equivalent or little higher than 0 $cmH_2O$;

providing a pressure component at a frequency comprised between 5 and 10 Hz and amplitude comprised between 2 and 4 $cmH_2O$;

inflation series (progressive increase of the positive end-expiratory pressure) and sampling in some predetermined pressure values (samples from 100 to 106); the variable positive end expiratory pressure (PEEP) is increased until a maxim prefixed value has been reached or until said end expiratory reactance (Xee) start to decreasing;

empirical verification of recruitment (samples from 100 to 103 of FIG. 3) or non-recruitment (FIG. 2) and of the occurrence of overdistension (samples 104 to 106 of FIG. 3);

deflation series (progressive decrease of the positive end-expiratory pressure) and sampling in some predetermined pressure values (samples from 107 to 112); the variable positive end expiratory pressure (PEEP) is decreased until a minimum prefixed value has been reached or until said end expiratory reactance (Xexp) start to decreasing;

empirical verification of the derecruitment (samples from 111 and 112 of FIG. 2) or non derecruitment (FIG. 2) situation;

identification of the optimal positive pressure, which is equivalent to the maximum value of end-expiratory reactance (Xee) during the deflation series (sample 110);

rising positive end-expiratory pressure to the maximum value reached during the inflation series;

finally, the positive end-expiratory pressure is set to the optimal value.

When positive end-expiratory pressure (PEEP) is set to the optimal value, the amplitude of the pressure waveform (ΔP) or the tidal volume (Vt) can be adjusted as follows.

Setting amplitude of the pressure waveform (ΔP) or tidal volume (Vt) to a value that is for sure higher than that needed by the patient (eg ΔP=30 cmH$_2$O or Vt=12 ml/kg of body weight);

Progressive decrease of the pressure waveform ΔP or the tidal volume Vt (for example in steps of 2 cmH$_2$O or 2 ml/kg of body weight) and sampling end-inspiratory reactance (Xei) at each step until Xei is higher of a given threshold.

As a variant the end-point for decreasing ΔP or tidal volume is that the difference between end-expiratory reactance (Xee) and end-inspiratory reactance (Xee) is smaller than a given threshold.

Such a procedure takes a few minutes and only requires a partial alteration of the respiration of the patient 2.

The pressure waveform (ΔP), that is the pressure variation between the inspiration and the expiration, or the tidal volume (Vt), that is the lung volume representing the normal volume of air displaced between normal inspiration and expiration, are applied to the patient by means of the ventilator 3.

A variant of the apparatus 1 may be made, according to which the electronic processor 12 also controls the ventilator 3 and sets the positive end-expiratory pressure thereof, and may therefore carry out the cycle of samplings in an automatic manner.

Furthermore, algorithms allowing to identify the presence of derecruitment on the basis of the analysis of the graph resulting from the samplings and recognise the maximum value (sample 110) of expiratory reactance may be implemented.

Well-known computing algorithms may also be used to obtain the maximum value of the expiratory respiratory reactance.

A computerised mechanical ventilator may also be made which, as well as imposing the respiratory flow, further allows to autonomously generate the additional pressure component, which in the suggested embodiment, is due to the speaker 15.

The invention also relates to a procedure for the detection of the optimal positive end-expiratory pressure in the course of respiration by means of a mechanical ventilator (3), which comprises the generation of a pressure stimulus ($P^{stim}$) with frequency components higher than the respiratory rate, and the following steps:

setting of the positive end-expiratory pressure to a value near 0 cmH$_2$O;

providing a pressure component at a frequency comprised between 5 and 10 Hz and amplitude comprised between 2 and 4 cmH$_2$O;

pressure (P) and flow (Flow) sampling and computing of the associated end-expiratory reactance (Xee) for increasing values of positive end-expiratory pressure (PEEP);

verifying recruitment and the occurrence of overdistension from the analysis of the resulting values of end-expiratory reactance (Xee). The increasing of the positive end expiratory pressure (PEEP) can be terminated at a predetermined maximum value of end-expiratory pressure (PEEP) or when the end expiratory reactance (Xee) start to decreasing (sample 105);

pressure (P) and flow (Flow) sampling and computing of the associated end-expiratory reactance (Xee) for decreasing values of positive end-expiratory pressure (PEEP); the decreasing of the positive end expiratory pressure (PEEP) can be terminated at a predetermined minimum value of end-expiratory pressure (PEEP) or when the end expiratory reactance (Xee) start to decreasing (sample 111);

verifying the derecruitment from the analysis of the resulting values of end-expiratory reactance (Xee);

identifying the optimal positive end-expiratory pressure (PEEP) (110);

rising positive end-expiratory pressure (PEEP) to the maximum level reached during the inflation series for few minutes (eg 2 minutes) to reverse the derecruitment produced by lowering positive end-expiratory pressure (PEEP) below optimal value;

setting the optimal positive end-expiratory pressure (PEEP) (3);

and further preferably comprising the steps of setting amplitude of the pressure waveform (ΔP) or tidal volume (Vt) to a value that is for sure higher than that needed by the patient (eg ΔP=30 cmH$_2$O or Vt=12 ml/kg of body weight);

decreasing ΔP or Vt in a stepwise fashion (for example in steps of 2 cmH$_2$O or 2 ml/kg of body weight) and sampling end-inspiratory reactance (Xei) at each step until Xei is higher of a given threshold or the difference between end-expiratory reactance (Xee) and end-inspiratory reactance (Xee) is smaller than a given threshold.

Such a procedure may also be integrated with a breath by breath monitoring step to detect derecruitment phenomena in the course of time and identify the best time for a new recruitment manoeuvre.

A procedure may also be used, allowing to detect the optimal continuous distension pressure in the course of the high frequency oscillatory ventilation using a similar approach described above to determine the optimal PEEP (in this application the CDP has the same role as the PEEP).

An algorithm, is now described for the computation of end-expiratory reactance (Xee) and of end-inspiratory reactance (Xei) that may be implemented for instance in the electronic processor 12.

The pressure P to which the patient is subjected, measured by the use of the above said devices (transducer 10, analogue-digital convertor 11, electronic processor 12) is divided, by the use of known digital filters, so as to obtain the respiratory component $P^{resp}$ imposed by the mechanical ventilator 3 and the additional component $P^{stim}$.

Similarly, the air flow $Flow^{tot}$, measured by the use of the above said devices (pneumotachograph 8, transducer 9, analogue-digital convertor 11, electronic processor 12) is divided in the low frequency component $Flow^{resp}$ and the high frequency component $Flow^{stim}$.

The periods of time during which an inspiration and an expiration occur may be obtained from the $\text{Flow}^{resp}$ analysis. Inspiration is associated to $\text{Flow}^{resp} > 0$, while expiration is associated to $\text{Flow}^{resp} < 0$ End-expiratory reactance (Xee) can be obtained as the average of reactance points measured in the period of time when respiratory flow ($\text{Flow}^{resp}$) is 0 and respiratory pressure ($\text{P}^{resp}$) is stable at positive end at end-expiratory pressure (PEEP) (period of time between ta and tb in FIGS. 4 and 9). For example ta can be picked one cycle of the stimulating pressure after the steep pressure drop and tb one cycle before the onset of pressure rise (FIG. 6). The identification of this bit of the expiratory phase of the breathing cycle is particularly important when the frequency content of the respiratory components of pressure ($\text{P}^{resp}$) and flow ($\text{Flow}^{resp}$) includes the range of frequency of the stimulation signal ($\text{P}^{stim}$ and $\text{Flow}^{stim}$). A period of time of at least 3 cycles of the stimulating oscillation is required to obtain Xee. If this is not the case during the regular respiratory support the expiratory time needs to be increased or short end-expiratory pause must be performed.

Similarly, end-inspiratory reactance (Xei) can be obtained as the average of reactance points measured in the period of time when respiratory flow ($\text{Flow}^{resp}$) is 0 and respiratory pressure ($\text{P}^{resp}$) is stable at the maximum value (period of time between tc and td in FIGS. 4 and 9). For example tc can be picked one cycle of the stimulating pressure after the pressure has reached the maximum value and td one cycle before pressure starts to drop (FIG. 6). The identification of this bit of the inspiratory phase of the breathing cycle is particularly important when the frequency content of the respiratory components of pressure ($\text{P}^{resp}$) and flow ($\text{Flow}^{resp}$) includes the range of frequency of the stimulation signal ($\text{P}^{stim}$ and $\text{Flow}^{stim}$). A period of time of at least 3 cycles of the stimulating oscillation is required to obtain Xei. If this is not the case during the regular respiratory support the expiratory time needs to be increased or short end-inspiratory pause must be performed.

The computation of reactance (Xrs) is simply obtained by means of the average of the instantaneous values of reactance (Xrs). Such an average may be obtained in an end-expiratory period, that is, with reference to FIGS. 4 and 9, in the time period between ta and tb separately.

The invention claimed is:

1. An apparatus (1) for respiratory support and non-invasive detection of alveolar recruitment/derecruitment for patients (2) suffering from respiratory failure, said apparatus (1) comprising means (3) for providing a pressure component ($\text{P}^{resp}$); means (15) for adding an additional pressure component ($\text{P}^{stim}$) at a frequency comprised between 5 and 10 Hz with a pressure comprised between 2 and 4 cm $H_2O$; conduits (5, 6, 7, 20, 21) for the passage of said pressure component ($\text{P}^{resp}$) and said additional pressure component ($\text{P}^{stim}$) from and to the airways of a patient (2); transducers, applied to said conduits, of pressure (9, 10) to electric signals; transducers, applied to said conduits, of flow (8) to electric signals and computing means (12) for providing a variable positive end-expiratory pressure (PEEP) to said patient (2); processing said electric signals so as to obtain a value of the end-expiratory reactance (Xee), at the varying of the value of said positive end-expiratory pressure (PEEP), and defining a state of pulmonary recruitment, as the value of the positive end-expiratory pressure (PEEP) which corresponds to a point of maximum end-expiratory reactance (Xee).

2. An apparatus according to claim 1, wherein said means (3) for providing a pressure component ($\text{P}^{resp}$) comprise a mechanical ventilator (3) allowing imposition of inspiration/expiration functions, and a settable positive end-expiratory pressure (PEEP).

3. An apparatus according to claim 1, wherein said means (15) for adding an additional pressure component ($\text{P}^{stim}$) comprise a high frequency oscillating ventilator allowing imposition of a periodic pressure having a frequency and an amplitude suitable to allow obtaining inspiratory reactance.

4. An apparatus according to claim 1 wherein said computing means (12) automatically controls the settings of said means (3) for providing a pressure component ($\text{P}^{resp}$) allowing carrying out the respiratory functions, said computing means (12) being provided with algorithms adapted to determine the maximum value of the end-expiratory reactance (Xee).

5. An apparatus according claim 1 wherein said means (15) for adding an additional pressure component ($\text{P}^{stim}$) comprise a speaker (15) fitted to at least one of said conduits (5).

6. An apparatus according to claim 1 wherein said means (15) for adding an additional pressure component ($\text{P}^{stim}$) comprise a modulating valve fitted to at least one of said conduits (5).

7. An apparatus according to claim 1 wherein said means (3) for providing a pressure component ($\text{P}^{resp}$) provide a pressure waveform ($\Delta P$) greater than 30 cmH$_2$O or a tidal volume (Vt) greater of 12 ml/kg of body weight; said computing means (12) provide a progressive decreasing of said pressure waveform ($\Delta P$) or said tidal volume (Vt) in some steps; said computing means (12) calculates an end-inspiratory reactance (Xei) at each step until the end-inspiratory reactance Xei is higher of a given threshold or until the difference between the end-expiratory reactance (Xee) and the end-inspiratory reactance (Xei) is smaller than a given threshold.

* * * * *